US 8,126,302 B2

(12) United States Patent
Rowe et al.

(10) Patent No.: US 8,126,302 B2
(45) Date of Patent: Feb. 28, 2012

(54) METHOD AND SYSTEM FOR CORRECTING AN OPTICAL BEAM

(75) Inventors: T. Scott Rowe, Dana Point, CA (US); Alexander N. Artsyukhovich, Dana Point, CA (US)

(73) Assignee: Novartis AG, Basel (CH)

( * ) Notice: Subject to any disclaimer, the term of this patent is extended or adjusted under 35 U.S.C. 154(b) by 911 days.

(21) Appl. No.: 11/692,508

(22) Filed: Mar. 28, 2007

(65) Prior Publication Data

US 2007/0268720 A1 Nov. 22, 2007

Related U.S. Application Data

(60) Provisional application No. 60/787,969, filed on Mar. 31, 2006.

(51) Int. Cl.
*G02B 6/32* (2006.01)
*G02B 6/26* (2006.01)
(52) U.S. Cl. ............................................ 385/33; 385/39
(58) Field of Classification Search ................... 385/33, 385/39
See application file for complete search history.

(56) References Cited

U.S. PATENT DOCUMENTS

| | | | | |
|---|---|---|---|---|
| 4,275,288 A | * | 6/1981 | Makosch et al. | 219/121.75 |
| 4,542,956 A | * | 9/1985 | McCrickerd | 385/33 |
| 4,729,621 A | | 3/1988 | Edelman | |
| 5,336,216 A | * | 8/1994 | Dewey | 606/4 |
| 5,357,312 A | | 10/1994 | Tounai | |
| 5,405,659 A | * | 4/1995 | Fernandez | 427/596 |
| 5,550,367 A | * | 8/1996 | Plesko | 235/462.22 |
| 5,754,719 A | | 5/1998 | Chen et al. | |
| 6,587,276 B2 | * | 7/2003 | Daniell | 359/622 |
| 6,628,877 B2 | * | 9/2003 | Dugan et al. | 385/129 |
| 6,690,702 B1 | * | 2/2004 | Ohmi et al. | 372/57 |
| 6,721,101 B2 | * | 4/2004 | Daniell | 359/626 |
| 6,928,239 B2 | * | 8/2005 | Fukui | 396/61 |
| 7,102,700 B1 | * | 9/2006 | Pease et al. | 348/744 |
| 7,142,257 B2 | * | 11/2006 | Callison et al. | 348/744 |
| 7,174,067 B2 | * | 2/2007 | Murshid et al. | 385/31 |
| 7,292,323 B2 | * | 11/2007 | Artsyukhovich et al. | 356/73.1 |
| 7,418,172 B2 | * | 8/2008 | Tanaka et al. | 385/39 |
| 7,474,339 B2 | * | 1/2009 | Hoshuyama | 348/223.1 |
| 7,502,178 B2 | * | 3/2009 | Shenderova et al. | 359/742 |
| 7,599,591 B2 | * | 10/2009 | Andersen et al. | 385/115 |
| 7,639,909 B2 | * | 12/2009 | Murshid et al. | 385/31 |
| 2002/0180869 A1 | * | 12/2002 | Callison et al. | 348/203 |
| 2003/0112523 A1 | * | 6/2003 | Daniell | 359/626 |
| 2004/0213514 A1 | * | 10/2004 | Tanaka et al. | 385/31 |
| 2005/0046944 A1 | * | 3/2005 | Shenderova et al. | 359/565 |
| 2005/0117209 A1 | | 6/2005 | Moller et al. | |

(Continued)

FOREIGN PATENT DOCUMENTS

EP 0687956 11/2007

(Continued)

*Primary Examiner* — K. Cyrus Kianni
(74) *Attorney, Agent, or Firm* — Keiko Ichiye

(57) ABSTRACT

Embodiments of the present invention provide a system and method for shaping an annular focal spot pattern to allow for more efficient optical coupling to a small gauge optical fiber. An embodiment of the present invention can include an illumination source operable to transmit an optical beam along an optical path, an optical fiber, and a correcting element positioned in the optical path between the illumination source and the optical fiber, the correcting element configured to reshape the optical beam to increase an amount of light received by the optical fiber.

12 Claims, 6 Drawing Sheets

U.S. PATENT DOCUMENTS

| | | |
|---|---|---|
| 2006/0033926 A1 | 2/2006 | Artsyukhovich et al. |
| 2006/0103835 A1* | 5/2006 | Artsyukhovich et al. .... 356/73.1 |
| 2007/0024836 A1* | 2/2007 | Singer et al. .................... 355/67 |
| 2007/0085936 A1* | 4/2007 | Callison et al. ............... 348/744 |
| 2007/0189664 A1* | 8/2007 | Andersen et al. ............... 385/25 |
| 2008/0230723 A1* | 9/2008 | Tanaka et al. .............. 250/492.2 |

FOREIGN PATENT DOCUMENTS

| | | | |
|---|---|---|---|
| JP | 2001017380 A | * | 1/2001 |
| WO | WO9009607 | | 8/1990 |
| WO | WO2005016118 | | 2/2005 |
| WO | WO2006053273 | | 5/2006 |

\* cited by examiner

Single-zone Axicon (optimum = -8°)

Multi-zone Axicon (optima shown below)

ZONE 1, Tilt = -9 deg
ZONE 2, Tilt = -6 deg
ZONE 3, Tilt = -3 deg
ZONE 4, Tilt = +1 deg
ZONE 5, Tilt = 0 deg
ZONE 6, Tilt = 0 deg

METHOD AND SYSTEM FOR CORRECTING AN OPTICAL BEAM

CROSS-REFERENCE TO RELATED APPLICATIONS

This application claims priority under 35 U.S.C. §119 to U.S. Provisional Patent Application No. 60/787,969, filed Mar. 31, 2006, the entire contents of which are incorporated herein by reference.

TECHNICAL FIELD OF THE INVENTION

The present invention relates generally to the field of illumination systems. In particular, the present invention relates to ophthalmic illumination systems and, more particularly, to a method and system for prismatic correction of an optical beam in an ophthalmic illumination system to improve coupling of the optical beam to a small diameter optical fiber.

BACKGROUND OF THE INVENTION

Many ophthalmic surgical procedures require illuminating a portion of a patient's eye so that a surgeon can observe the surgical site. Various different types of instruments are known and available for use by an ophthalmic surgeon to illuminate the interior of the eye. The handheld (probe) portion of a typical ophthalmic illuminator comprises a handle having a projecting tip and a length of optical fiber that enters a proximal end of the handle and passes through the handle and the tip to a distal end of the tip, from which light traveling along the optical fiber can project. The proximal end of the optical fiber can be positioned adjacent to a light source, such as in a high brightness illuminator, as known to those having skill in the art, to provide the light that is transmitted through the fiber. These types of handheld illuminators are typically used by inserting the probe tip through a small incision in the eye. In this way, light from the illuminator light source is carried along the optical fiber, through the handpiece and emitted from the distal end of the probe (fiber) to illuminate the surgical site for the surgeon. Ophthalmic illuminators that use a length of optical fiber to carry and direct light from a light source to a surgical site are well known in the art.

Such an ophthalmic illumination system typically comprises a handheld portion, or probe, to deliver illumination from a light source housed in an enclosure, the enclosure typically housing the light source and associated optics that guide light from the light source to the optical fiber of the probe, a power supply, electronics with signal processing, and associated connectors, displays and other interfaces as known in the art. While some ophthalmic illumination systems use other types of lamps as a light source, a preferred light source is a xenon lamp. Some prior art xenon lamps exists that use quartz for the lamp body material. However, quartz has been found to be unstable at the high operating temperature of typical xenon lamps and has a tendency to fail and sometimes explode. This is because as the quartz lamp body ages, the quartz crystallizes, cracks, and is then susceptible to failure. As a result, these prior art xenon lamp illuminators contain the xenon lamp and quartz lamp body within a steel housing. Ceramic lamp bodies, on the other hand, have been found safe for use in the high temperature environment of a xenon lamp. Most modern ophthalmic illumination systems using xenon lamps thus typically employ a ceramic body.

However, unlike with a quartz lamp body, the electrodes of a ceramic-bodied xenon lamp typically intrude into the lamp's optical path. This disadvantage is not present in prior art quartz-bodied lamps because the lamp electrodes are vertical and do not invade into the optical path. However, in a ceramic body, the electrodes are placed such that they interfere with the center portion of the lamp's optical beam, resulting in a "donut" shaped optical beam instead of a more homogenous "dot-shaped" beam. The reflector, electrodes and their associated supports cast shadows within the optical beam resulting in a focal spot having a donut shape, as shown in FIG. 1.

The annular-shaped focal spot of ceramic-bodied high-pressure xenon lamps has until recently not been a problem for ophthalmic illumination systems because these prior art systems typically use fiber bundles (e.g., 3 to 6 mm fiber bundles) to receive the annular focal spot and transmit the received light from the light source to a surgical site. However, with the advent of small core-diameter optical fibers (e.g., about 3 mm diameter) such as can be used with the Alcon High Brightness Illuminator, manufactured by Alcon Laboratories, Inc., of Irvine, Calif., for use in ophthalmic endo-illumination systems, the annular focal spot of prior art xenon lamps is in conflict with the desire to couple the xenon lamp output into a small core optical fiber. This is particularly so because these modern endo-illuminators typically use a single fiber to guide and direct light from the light source to the surgical site. Such small core optical fiber endo-illuminators are desirable because they require a smaller incision and thus lessen trauma and possible damage to a patient's eye.

Focusing the output from a xenon light source in these prior art ophthalmic illumination systems into a small core diameter optical fiber is thus not only difficult, but results in a poor optical-coupling to the optical fiber. Further, the annular focal spot from such an illuminator is typically approximately 1 mm in diameter. Focusing this annular focal spot into an approximately half a millimeter fiber (e.g., a typical 25-gauge optical fiber) results in an irregular intensity distribution of the transmitted light. Note that for a 20 gauge optical fiber the problem is not as great because the entire annular focal spot can fit within the 20-gauge optical fiber diameter.

Prior art ophthalmic illumination systems have attempted to solve this problem by defocusing the annular focal spot to direct some light into the central portion of the focal spot. The problem with this approach is that as the focal spot is defocused, the intensity of the transmitted light decreases because less of the light from the light source is directed into the optical fibers. Further, although prior art ophthalmic illumination systems do not focus the output of the xenon lamp into a single optical fiber, when focusing the output of the xenon lamp into a fiber bundle, prior art illuminators have attempted to beam-shape the output of the xenon lamp by the use of diffractive optical elements. The problem with the use of diffractive elements is that they are sensitive to changes in the light source beam, and the output from a xenon lamp changes significantly as the lamp ages. Also, inexpensive custom-made diffractive elements are typically made of plastic, which can be damaged relatively easily by a high intensity optical beam originating at a xenon lamp.

Therefore, a need exists for a method and system for correcting an optical beam that can shape the annular focal spot pattern from a high pressure ceramic xenon lamp into a focal spot with quasi-Gaussian intensity distribution for efficient optical fiber coupling. Further still, there is a need for such a method and system for correcting an optical beam that will provide stable correction as a lamp source ages and that can improve fiber coupling efficiency of the lamp source output into a small (e.g., ≦3 mm diameter) optical fiber, such as 20 and 25 gauge optical fibers.

BRIEF SUMMARY OF THE INVENTION

The embodiments of the method and system for correcting an optical beam of the present invention substantially meet these needs and others. One embodiment of the system for correcting an optical beam of this invention comprises: an illumination source operable to transmit an optical beam along an optical path, an optical fiber and a correcting element positioned in the optical path between the illumination source and the optical fiber, the correcting element configured to reshape the optical beam to increase an amount of light received by the optical fiber. The correcting element may reshape the optical beam from having an annular focal spot to having a focal spot with a more Gaussian intensity distribution than the annular focal spot.

Other embodiments of the present invention can include a method for correcting an optical beam in accordance with the teachings of this invention. One embodiment of the method comprises: generating an optical beam using an illumination source, directing the optical beam to a correcting element, reshaping the optical beam using the correcting element to have a focal spot with a more Gaussian intensity distribution than prior to the correcting element, optically coupling the shaped optical beam to an optical fiber and directing the optical beam to a surgical site.

Another embodiment of the present invention can comprise an optical correcting system for a high-pressure xenon lamp illuminator optical coupling comprising: an illumination source, a first mirror optically coupled to the illumination source to receive an optical beam from the illumination source, a second mirror optically coupled to the first mirror to receive the optical beam from the first mirror, a first correcting element in optical communication with the illumination source, wherein the first correcting element reshapes the optical beam to have a focal spot with a more Gaussian intensity distribution than upstream of the correcting element and a first optical fiber port in optical communication with the first correcting element and operable to be coupled to the proximal end of an optical fiber.

Embodiments of this invention can be implemented within a surgical machine or system for use in ophthalmic or other surgery. In particular, it is contemplated that the method and system for correcting an optical beam of this invention can be implemented in, or incorporated into, any ophthalmic illumination system in which it is desirable to efficiently couple a xenon light source optical beam to a small diameter optical fiber. Other uses for the method and system for correcting prismatic an optical beam in accordance with the teachings of this invention will be apparent to those having skill in the art.

BRIEF DESCRIPTION OF THE SEVERAL VIEWS OF THE DRAWINGS

A more complete understanding of the present invention and the advantages thereof may be acquired by referring to the following description, taken in conjunction with the accompanying drawings, in which like reference numbers indicate like features and wherein.

DETAILED DESCRIPTION OF THE INVENTION

Preferred embodiments of the present invention are illustrated in the FIGUREs, like numerals being used to refer to like and corresponding parts of the various drawings.

The various embodiments of the method and system for prismatic correction of an optical beam of this invention provide for correcting the annular focal spot pattern of a high-pressure xenon lamp for more efficient optical coupling to a small gauge optical fiber. The embodiments of this invention can reshape the optical beam profile to transform the annular focal spot into a more bell shaped (Gaussian) intensity distribution that will more efficiently couple the output of the xenon lamp into a small diameter optical fiber.

Figure 1:
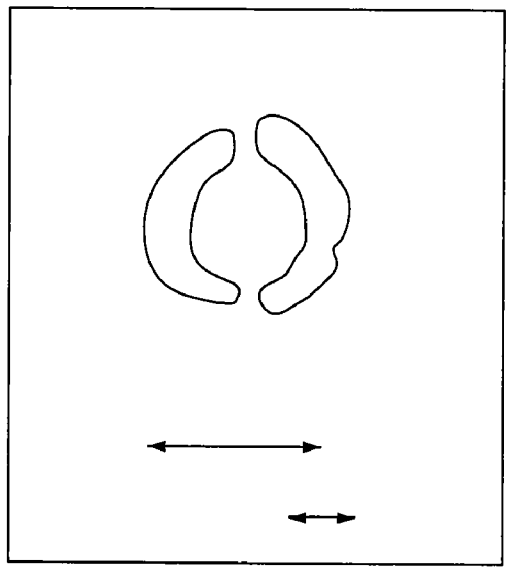
FIGS. 1 and 2A show a typical focal spot intensity distribution of an optical beam from a high output ceramic-bodied xenon lamp.
Figure 2A:
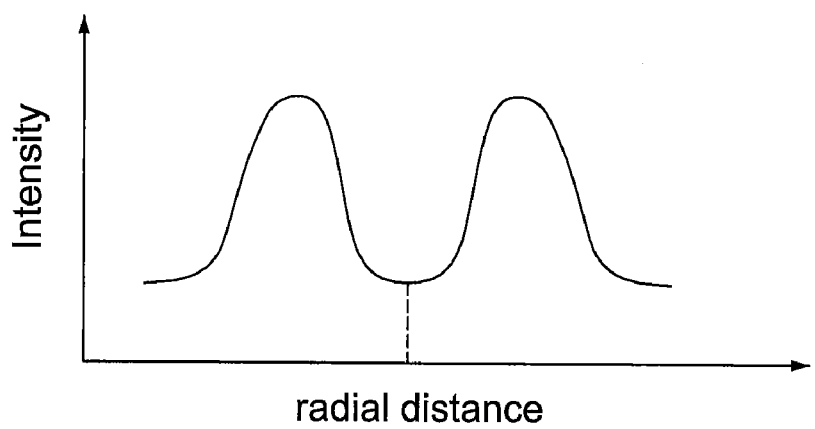
Figure 2B:
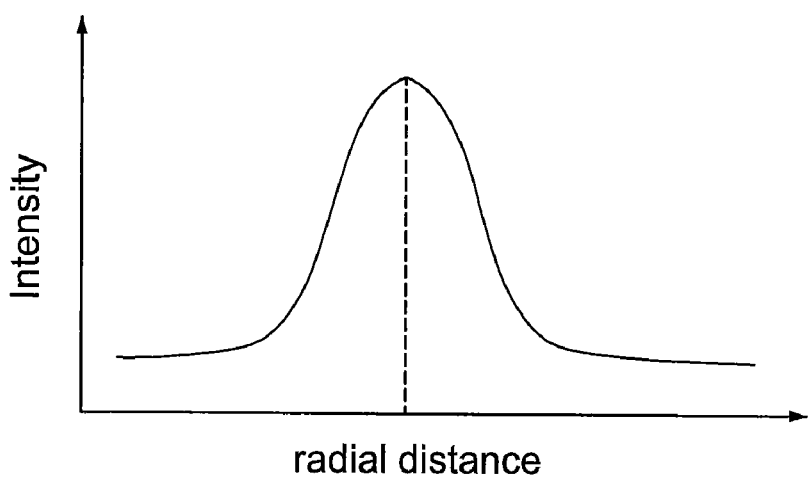
FIG. 2B shows a preferred Gaussian focal spot intensity distribution as can be achieved using embodiments of the present invention.

As can be seen in FIGS. 1 and 2A, the typical focal spot intensity distribution of an optical beam from a high output ceramic-bodied xenon lamp is uneven, with its greatest intensity toward the edges of the optical beam and lesser intensity toward the center. This intensity distribution is inefficient for directing (coupling) a homogenous light beam to a small diameter optical fiber in, for example, an endo-illuminator probe, and will result in a light output from the endo-illuminator probe that is brighter along the edges and dimmer in the center, which is not the preferred distribution for illuminating a surgical site. It is preferable to have a uniform intensity distribution, or at least a distribution such as in FIG. 2B that is more Gaussian in nature with greater intensity in the center and intensity decreasing outward toward the edges of the beam. The various embodiments of the present invention can reshape the intensity distribution of an optical beam in an ophthalmic illuminator from a distribution such as in FIG. 2A, to a distribution more closely related to that of FIG. 2B by providing an optical correcting element (e.g., a prismatic correcting element) in the optical path from the light source upstream of the endo-illuminator probe optical fiber proximal end. Further, the various embodiments of the present invention provide a method and system for correcting an optical beam that, unlike the prior art, can provide a stable, consistent optical beam output as the xenon illumination source ages.

Figure 3:
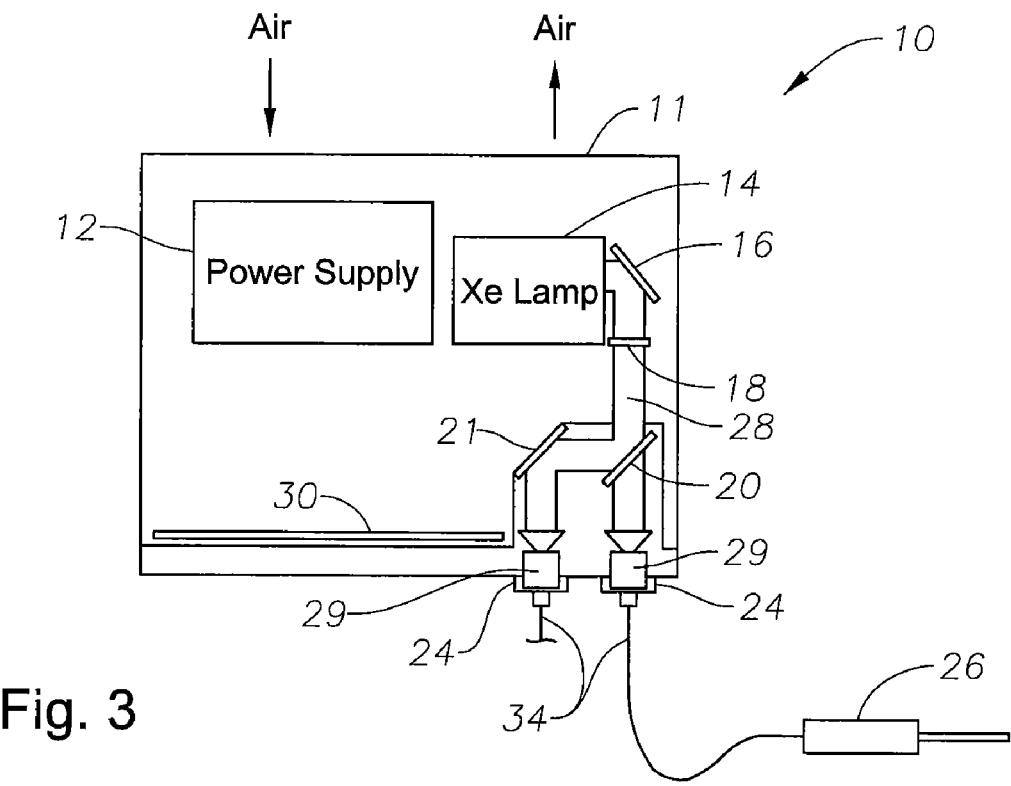
FIG. 3 is a simplified block diagram of a high-brightness ophthalmic illumination system incorporating an embodiment of the optical element for correcting an optical beam of the present invention.

FIG. 3 is a simplified block diagram of a high-brightness ophthalmic illumination system incorporating an embodiment of the optical element for correcting an optical beam of the present invention. Illuminator system 10 comprises power supply 12 and illumination source 14, cold mirror 16, a hot mirror 18, a beam splitter 20, mirror or beam splitter 21, optical fiber ports 24 and correcting elements 22. Illuminator system 10 can also include optical beam attenuators, such as those disclosed in pending U.S. application Ser. No. 11/204,305, which is hereby incorporated by reference in its entirety, for attenuating the optical beam from illumination source 14. Illuminator system 10 also can typically comprise one or more optical fiber probes 26, which comprise the handheld portion of the illuminator system 10, including optical fiber 34, which is optically coupled to the illumination source 14 within enclosure 11. High-brightness illumination system 10 is exemplary only and is not intended to limit the scope of the present invention in any way. The embodiments of the present invention can be used in any such ophthalmic high-brightness illuminator or in any system or machine in which it is desirable to efficiently couple the output of a xenon light source to a small gauge optical fiber.

Optical source 14 of illuminator system 10 comprises a xenon lamp as known to those having skill in the art. Xenon lamp 14 emits light beam 28, which is directed along the optical path comprising cold mirror 16, hot mirror 18, beam splitter 20, beam splitter 21, correcting elements 22 and optical fiber ports 24. In an embodiment including beam splitter 21, beam splitter 20 can be a 50/50 beam splitter and beam splitter 21 can be a 98/2 percent beam splitter. Cold mirror 16 and hot mirror 18 combine to remove the infrared components of light beams 28 (heat) and provide a "cool" visible light beam 28 to the downstream optical components, as will be known to those having skill in the art. Correcting elements 22 reshape optical beam 28 in the manner disclosed herein. Each correcting element 22 can be custom designed for its respective optical path and the two need not be identical, though they can be.

Although high-brightness illuminator system 10 is shown comprising two optical fiber ports 24, it will be obvious to those familiar with the art that a single optical fiber port 24 or multiple optical fiber ports 24 can be implemented within such a fiber optic illuminator system. In one embodiment, dual optical fiber ports 24 can comprise a 25 gauge optical fiber port and a 20 gauge optical fiber port. Illuminator system 10 further comprises a printed circuit board ("PCB") 30, or its electronic equivalent, to provide signal processing and control functions. PCB 30 can be implemented in any manner and configuration capable for performing the desired processing and control functions described herein, as will be apparent to those having skill in the art. Optical fiber ports 24 comprise a receptacle to receive the proximal end of an optical fiber probe 26 and its optical fiber 34, which are inserted into the high-brightness illuminator enclosure 11 and optically coupled to illumination source 14 to receive and direct light from illumination source 14 onto a desired site. Optical fiber ports 24 can further comprise coupling lenses 29, which can be Melles Griot LAG ØØ5 coupling lenses or similar aspherical coupling lenses for focusing light beam 28 onto the proximal end of optical fiber 34, as will be known to those having skill in the art.

Figure 4:
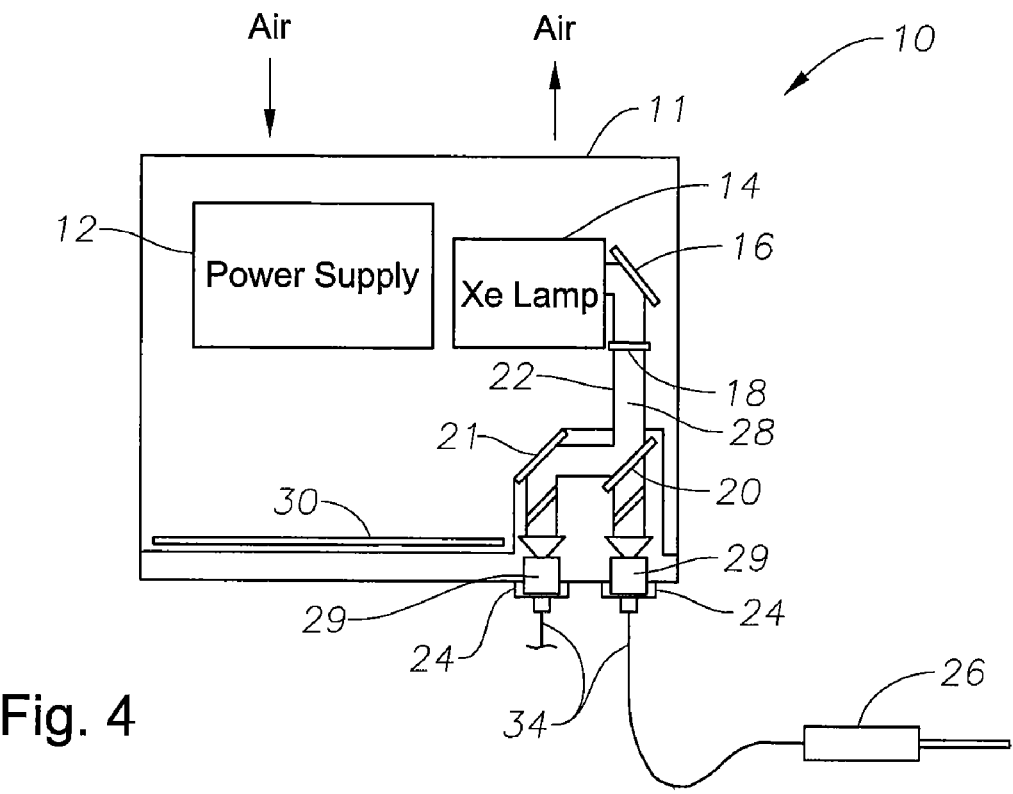
FIG. 4 shows a high brightness ophthalmic illumination system incorporating another embodiment of the present invention comprising a single correcting element 22 upstream of hot mirror 18, instead of the dual correcting elements 22 of FIG. 3.

The embodiments of the present invention provide a correcting element 22 upstream in the optical path before coupling lenses 29 in order to transform the annular focal spot from the xenon lamp into a Gaussian intensity profile focal spot. Correcting elements 22 provide beam shaping of light beam 28 and can in some embodiments comprise a beam-shaping module. Correcting element 22 can be an axiconic, isomorphic, or diffractive element, as will be known to those having skill in the art. Correcting element 22 can also comprise a Fresnel lens. Embodiments of the system for correcting an optical beam of this invention can comprise any such optical device that can be used to shape an annular focal spot into a focal spot having a more Gaussian intensity distribution as described herein. FIG. 4 shows another embodiment of such a system according to the present invention having a single correcting element 22 upstream of hot mirror 18, instead of the dual correcting elements 22 of FIG. 3. The embodiment of FIG. 4 is a lower cost alternative having almost the same performance characteristics as a dual correcting element 22 embodiment.

Figure 5:
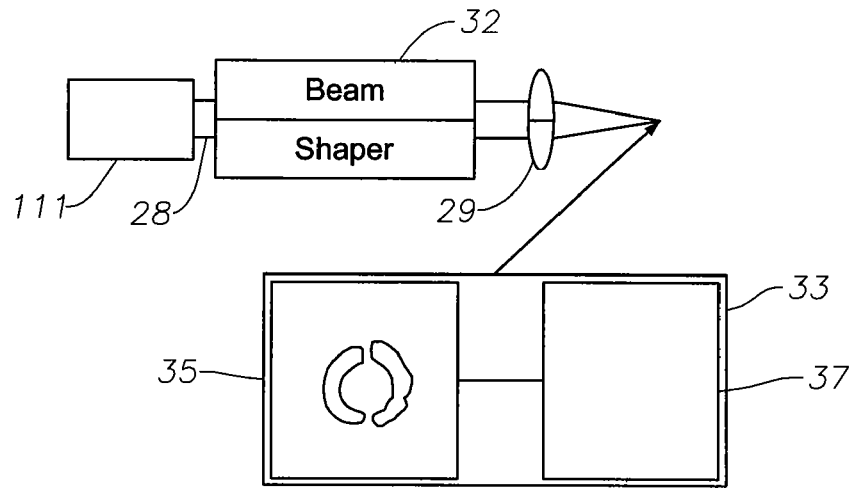
FIG. 5 is a diagrammatic representation illustrating the concept for beam shaping of optical beam 28 in accordance with the embodiments of the present invention.

FIG. 5 is a diagrammatic representation illustrating the concept for beam shaping of optical beam 28 in accordance with the embodiments of the present invention. Xenon light source 14 provides optical beam 28, which is directed into a beam shaper module 32 that transforms optical beam 28 in a manner as described herein. Reshaped optical beam 28 is provided to coupling lens 29, which focuses the reshaped beam 28 onto an optical fiber, such as optical fiber 34. The output from coupling lens 29, as shown in the blow-up 33, is transformed by beam shaper module 32 in combination with coupling lens 29 from an annular focal spot 35 to a more Gaussian focal spot 37.

Figure 6:
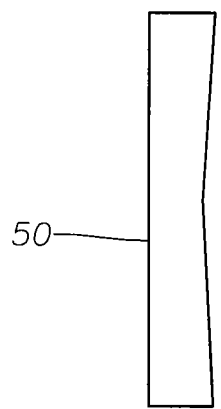
FIG. 6 is a diagrammatic representation of one embodiment of a correcting element 22 of this invention that comprises a single zone negative axicon 50.
Figure 7:
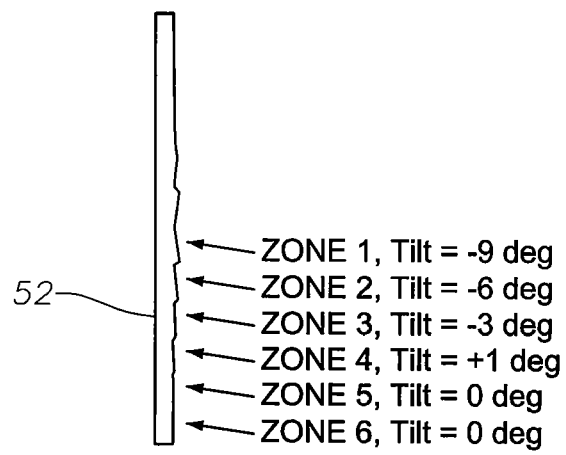
FIG. 7 is a diagrammatic representation of one embodiment of a correcting element 22 of this invention that comprises a multi-zone axicon 52.

FIG. 6 is a diagrammatic representation of one embodiment of a correcting element 22 that comprises a single zone negative axicon 50. An alternative embodiment is shown in FIG. 7 and comprises a multi-zone axicon 52. Both devices introduce prismatic correction to an optical beam 28 that shifts the optical beam from an annulus towards the annulus center. Because an axicon correcting element 22 is a figure of rotation of a regular prism, the prismatic angular is applied in a circular fashion, shifting all points on the annulus towards the center. A multi-zone axicon 52 provides better compensation since the optimal prismatic angle decreases with the distance of the beam from the center in the collimated xenon lamp output.

The embodiments of correcting element 22 shown in FIGS. 6 and 7 illustrate one set of angles for efficiently coupling the light output from the xenon lamp 14 into a narrow gauge optical fiber such as optical fiber 34. Using these axiconic elements with an ophthalmic illumination system such as that of FIGS. 3 and 4, improvements in coupling the output from xenon lamp 14 into an optical fiber 34 were calculated using an Advanced Systems Analysis ("ASAP") optical software model. The results are shown in Table 1 below.

TABLE 1

| | OPTICAL FIBER CAUGE | | | | | | | |
|---|---|---|---|---|---|---|---|---|
| | 20 G FIBER | | | | 25 G FIBER | | | |
| | Lamp age | | | | | | | |
| | 450 HRS | | 50 HRS | | 450 HRS | | 50 HRS | |
| Output Units | lm | % vs PS | lm | % vs PS | lM | % vs PS | lm | % vs PS |
| Lamp only | 24 | −4.0% | 56 | 124.0% | 8.4 | 40.0% | 20 | 233.3% |
| Lamp and Fresnel lens | 37.4 | 59.6% | 57 | 128.0% | 13.8 | 130.0% | 21 | 250.0% |
| Lamp and Axiconic lens | 31.5 | 26.0% | 53 | 112.0% | 11.6 | 93.3% | 20 | 233.3% |

ASAP optical software predictions of fiber coupling efficiency with single and multi-zone axicons.

As can be seen from Table 1, a considerable advantage is achieved for the case of an aged xenon lamp, assuring that the typical exponential decline of a Xenon lamp due to aging will be considerably slowed from that of ophthalmic illuminators in the prior art. This is an extremely desirable result that allows extending Xenon lamp life in a high-brightness illumination system such as the Alcon High-Brightness Illuminator manufactured by Alcon Laboratories, Inc. of Irvine, Calif.

In a typical ophthalmic illumination system 10 only a small fraction of the xenon lamp 14 output is coupled into the small gauge optical fibers of the endo-illuminator probe 26. This is because light from the xenon lamp 14 is typically lost in one of two places: (1) the xenon lamp is a spot light that illuminates the interior of the ophthalmic illumination system enclosure and not just the coupling lenses; and (2) conservation of energy and radiance limit how much light can be forced into an optical fiber.

Figure 8:
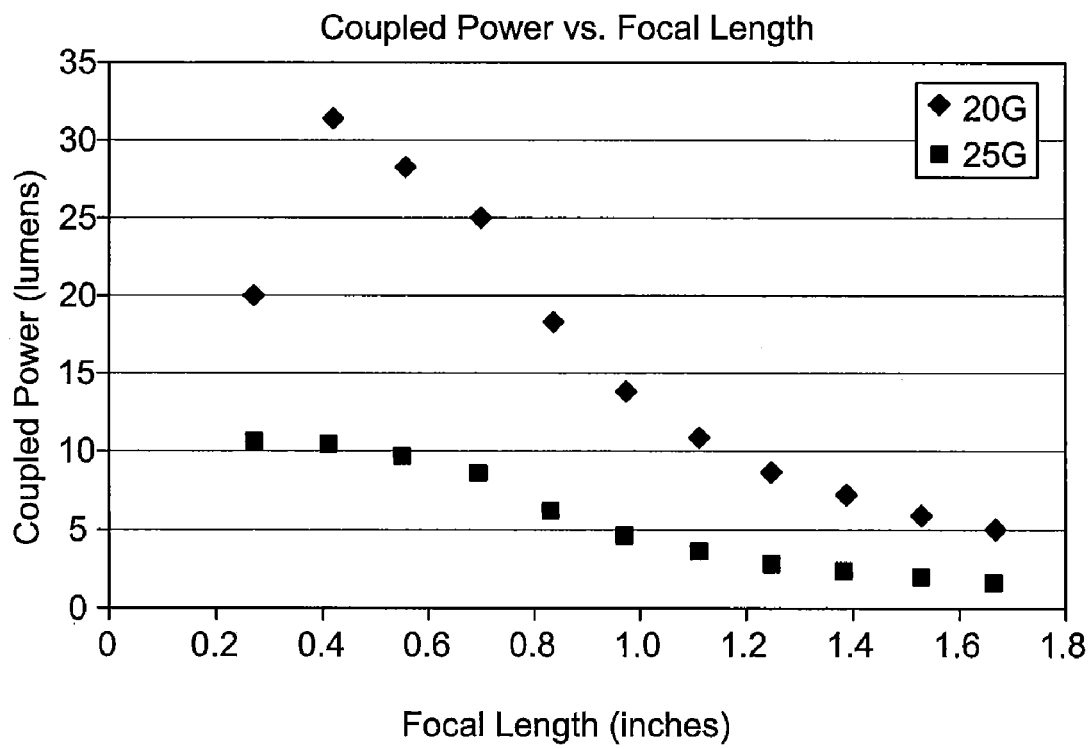
FIG. 8 is a graph of the coupled power vs. focal length for both 25 gauge and 20 gauge fibers in one experiment conducted according to the teachings of this invention.
Figure 9:
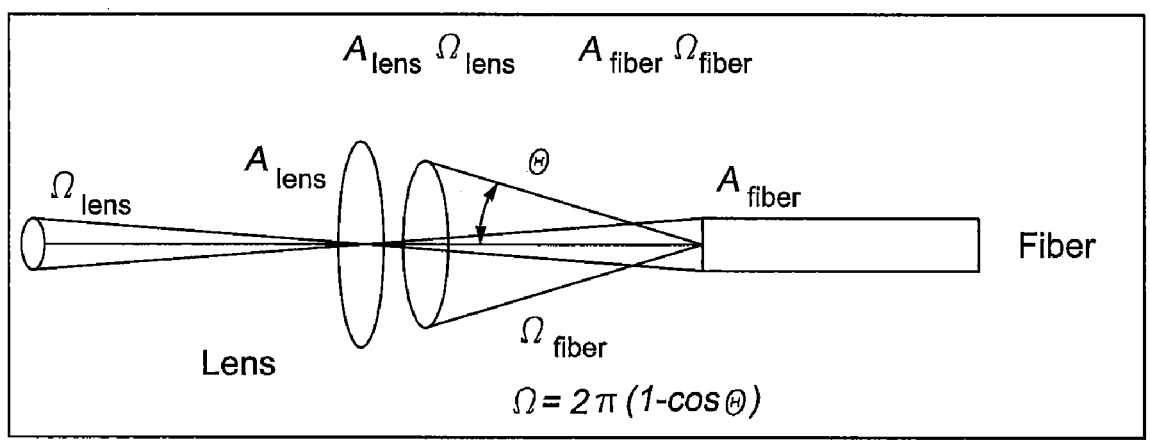
FIG. 9 is an illustration of the area-solid angle product for an optical fiber.

In one experiment, the power coupled into a narrow gauge optical fiber, such as a 20 gauge or 25 gauge optical fiber, was calculated and repeated for ten different coupling lens 29 focal lengths. FIG. 8 shows a graph of the coupled power vs. focal length for both 25 gauge and 20 gauge fibers resulting from this experiment. As can be seen from FIG. 8, only a small fraction of the lamp output is coupled into the optical fibers. As an example, in the system of FIGS. 3 and 4, the coupling lens 29 directly downstream of the 50/50 beam splitter receives, in one experiment, 105 lumens while the lens directly downstream of the 98/2% beam splitter received 71 lumens. Conservation of energy and radiance dictate that, referring also to FIG. 9:

$$A_{lens}\Omega_{lens}=A_{fiber}\Omega_{fiber}, \text{ where } \Omega=2\pi(1-\cos\theta) \quad \text{Eq. 1}$$

Using a 20 G optical fiber as an example, the optical fiber is the limit with an area-solid angle product equal to 5.6E−4 in$^2$−sr. Light incident on the optical fiber that exceeds this value will not couple into the optical fiber. With a 0.84 inch diameter coupling lens 29, of the light incident on the coupling lens 29 only the light within a 1 degree half angle will couple into the optical fiber. Unfortunately, the xenon lamp subtends a 1.95 degree half angle as seen from the coupling lens. The lamp output for a 1.95 degree half angle is 149 lumens while the lamp output for a half angle equal to 1 degree is 42 lumens. Therefore, only a fraction (42/149=0.282) or 30 lumens of the 105 lumens incident on the coupling lens 29 will couple into the 20 G fiber.

Since the fiber numerical aperture ultimately limits the cone of light coupled into an optical fiber and since an extremely small f-number is unrealistic, one alternative is to decrease the coupling lens 29 focal length to 0.73" in an effort to match the lens f-number and the fiber acceptance cone.

Figure 10:
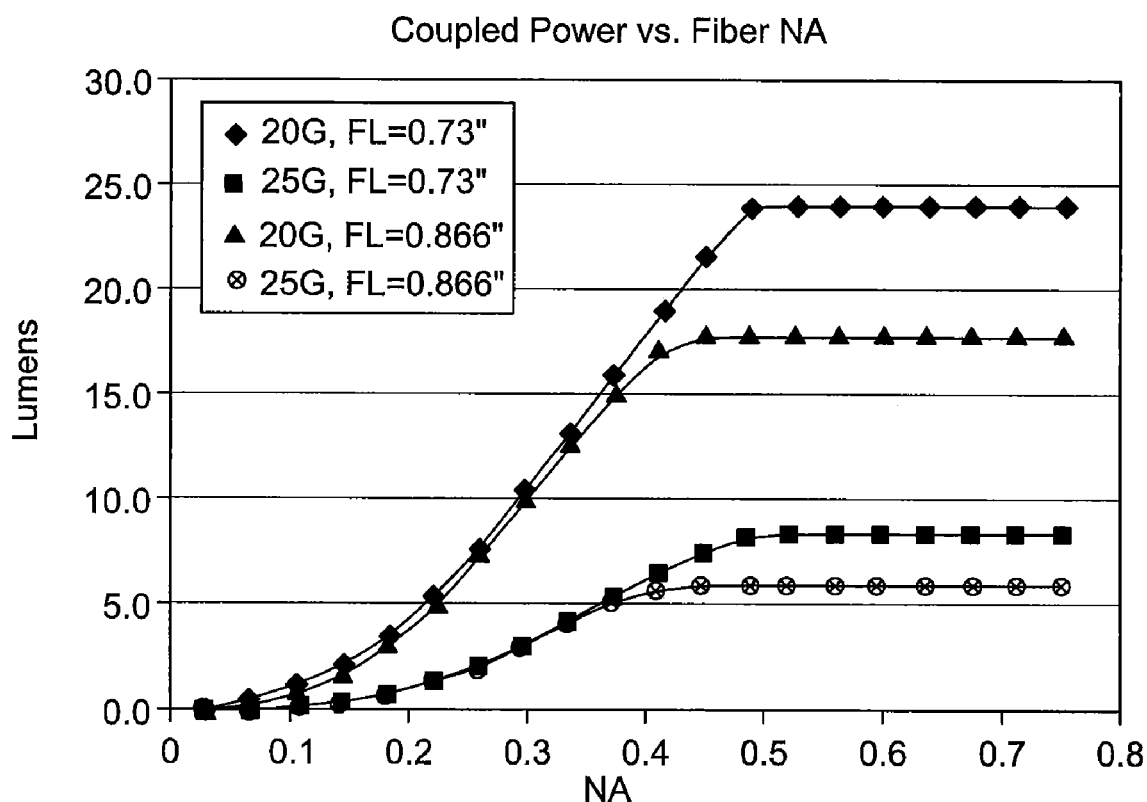
FIG. 10 is a graph showing coupled power vs. fiber numerical aperture for a baseline coupling lens design focal length (0.866") and for a focal length equal to 0.73"

FIG. 10 shows coupled power vs. fiber numerical aperture for the baseline design focal length (0.866") and for a focal length equal to 0.73".

Results when adding a Fresnel lens and an axiconic lens downstream of the xenon lamp are shown in Table 2. For this phase the Fresnel lens has a series of cone shaped segments. We chose a Fresnel lens diameter equal to 1.25" with a total of 6 zones. Table 2 shows the lamp 1 output power incident on the 6 zones.

TABLE 2

Lamp 1 output power vs. Fresnel zone.

| Zone Number | Power (lumens) |
|---|---|
| 1 | 149 |
| 2 | 315 |
| 3 | 286 |
| 4 | 112 |
| 5 | 21 |
| 6 | 6 |

Not only does the lamp output power vary with zone number, the angular distribution does also. The smaller the angular distribution the better coupling we will get into the fiber. To narrow lamp 1 angular distribution we adjusted the tilt angles individually for each Fresnel zone facet. In fact, we calculated the power coupled into the 20 G fiber as a function of Fresnel zone facet angle for all six zones (Table 3).

TABLE 3

Coupled power per Fresnel zone vs. facet tilt angle.

| | Fresnel Facet Tilt Angle (deg) | Coupled Power (lumens) |
|---|---|---|
| ZONE 1 | −12 | 1.5 |
| | −9 | 3.5 |
| | −6 | 2.6 |
| | −3 | 1.0 |
| | 0 | 0.2 |
| | 3 | 0.1 |
| | 6 | 0.1 |
| | 9 | 0.1 |
| | 12 | 0.2 |
| ZONE 2 | −12 | 0.6 |
| | −9 | 5.0 |
| | −6 | 12.0 |
| | −3 | 9.6 |
| | 0 | 5.8 |
| | 3 | 2.7 |
| | 6 | 0.7 |
| | 9 | 0.0 |

TABLE 3-continued

Coupled power per Fresnel zone vs. facet tilt angle.

| Zone | Fresnel Facet Tilt Angle (deg) | Coupled Power (lumens) |
|---|---|---|
|  | 12 | 0.1 |
|  | −4 | 14.1 |
|  | −3 | 16.0 |
|  | −2 | 15.5 |
|  | −1 | 13.6 |
| ZONE 3 | 0 | 12.0 |
|  | 1 | 10.2 |
|  | 2 | 8.8 |
|  | 3 | 7.4 |
|  | 4 | 5.9 |
|  | −2 | 3.7 |
|  | −1.5 | 4.2 |
|  | −1 | 4.4 |
|  | −0.5 | 4.4 |
| ZONE 4 | 0 | 4.6 |
|  | 0.5 | 4.7 |
|  | 1 | 4.8 |
|  | 1.5 | 4.5 |
|  | 2 | 4.4 |
|  | −20 | 0 |
|  | −15 | 0 |
|  | −10 | 0 |
|  | −5 | 0 |
| ZONE 5 | 0 | 0 |
|  | 5 | 0 |
|  | 10 | 0 |
|  | 15 | 0 |
|  | 20 | 0 |
|  | −20 | 0 |
|  | −15 | 0 |
|  | −10 | 0 |
|  | −5 | 0 |
| ZONE 6 | 0 | 0 |
|  | 5 | 0 |
|  | 10 | 0 |
|  | 15 | 0 |
|  | 20 | 0 |

Next we constructed a six zone Fresnel lens with the optimized facet angles from Table 3. The Fresnel lens increased the lamp 1 coupling from 24 lumens to 37.4 lumens for the 20 G fiber, but had essentially no impact on lamp 2 coupling for the 20 G fiber. Therefore, with the Fresnel lens in place there is less difference in coupling between the new and aged lamps.

Figure 11:
FIG. 11 shows a cross-section of one best performing axiconic design correcting element according to the present invention.

An axiconic is governed by six independent parameters: two coordinates for a point on the surface, two coordinates for the first conic focus, and two coordinates for the second conic focus. To determine whether or not an axiconic placed in front of a xenon lamp will improve coupling, we selected a point on the surfaces and then explored all combinations of 5 values for each of the remaining 4 independent axionic variable. In total we calculated coupling for 625 different axiconic solutions. FIG. 10 shows the family of axiconic surfaces that were explored. FIG. 11 shows a cross-section of one best performing axiconic design. The axiconic lens increased the lamp 1 coupling from 24 lumens to 31.5 lumens for the 20 G fiber and only slightly degrades lamp 2 coupling.

A parametric study vs. coupling lens focal length for a xenon lamp was also performed. The parametric study indicated that shorter focal lengths can theoretically improve coupling by up to 75%. In practice, aberrations and diffraction are likely to limit improvement. Next, we shortened the coupling lens focal length to 0.73" and then designed and added a Fresnel lens and then an axiconic lens in front of the xenon lamp. Table 4 summarizes the results. The Fresnel lens is the best performer. The Fresnel lens narrows the angular output of the source causing a larger fraction of the source power to strike the coupling lens within the angular subtense of the fiber. It may be possible to extend this angular preconditioning approach and increase coupling by adding a "pillow lens" structure (as seen on the tail-lamp of a car) to the flat side of the Fresnel lens. Note however, that with each coupling improvement the design becomes more sensitive to fabrication errors and changes in the lamp distribution with time.

TABLE 4

|  | Coupling Power (lumens) | | | |
|---|---|---|---|---|
|  | 20 G fiber Lamp 1 (Likely aged) | 20 G fiber Lamp 2 (Likely 50 hr) | 25 G fiber Lamp 1 (Likely aged) | 25 G fiber Lamp 2 (Likely 50 hr) |
| Lamp Only | 24 | 56 | 8.4 | 20 |
| Lamp and Fresnel Lems | 37.4 | 57 | 13.8 | 21 |
| Lamp and axiconic lens | 31.5 | 53 | 11.6 | 20 |

As can be seen from the examples provided herein, one preferred embodiment of correcting element 22 is a seven-zone Fresnel lens optimized for maximum coupling into a 25 gauge fiber, but other embodiments can comprise a 6, 7 or 8 zone Fresnel lens for coupling into a 20 gauge or 25 gauge fiber. In a preferred embodiment, a correcting element 22 can be positioned in each optical path leading to each port 24. An alternative embodiment can be a single correcting element 22 embodiment as shown in FIG. 4, in which a correcting element 22 is placed in the optical path before the 50/50 beam splitter and downstream from the hot mirror 18. Further, an embodiment of the present invention can comprise two correcting elements 22, as shown in FIG. 3, in which each correcting element 22 is custom fit to its optical path. This is to compensate, for example, for the fact that the beam splitters may not be completely symmetrical and could result in some slight changes to the optical beam 28 along each path. An embodiment in which correcting elements 22 are custom-fit can correct for such differences and other similar path-induced differences.

Figure 12:
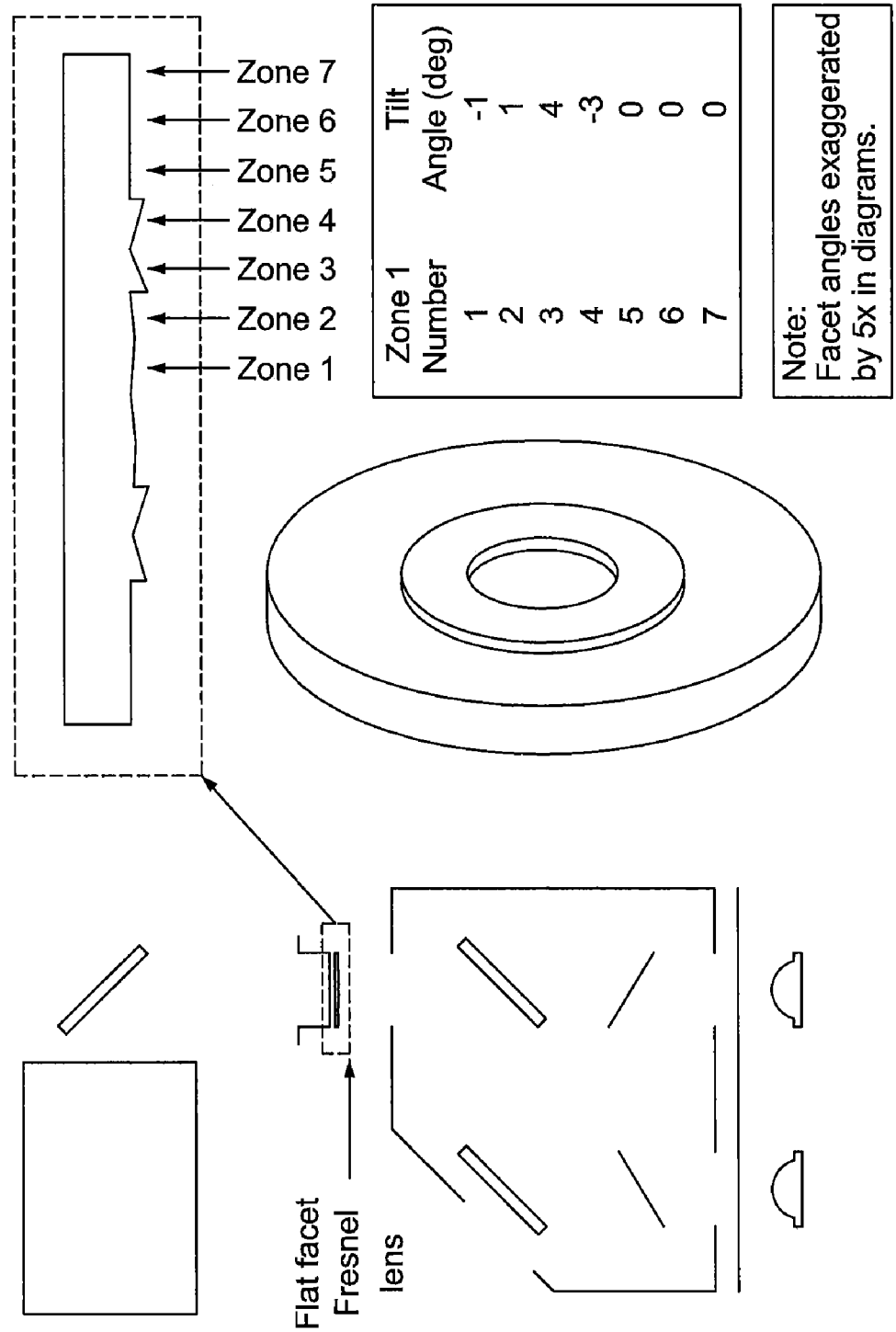
FIG. 12 is a diagrammatic representation of a seven-zone Fresnel lens embodiment of correcting element 22 of this invention.

FIG. 12 is a diagrammatic representation of a seven-zone Fresnel lens embodiment of correcting element 22, along with the accompanying tilt angles for each of the varying zones.

Various embodiments of the present invention thus provide for improved optical coupling of a xenon light source beam to a small gauge optical fiber. In particular, the embodiment of this invention can increase coupling efficiency into 20 and 25 gauge or smaller optical fibers. Further, the embodiments of this invention provide the ability to significantly reduce the decay in coupling efficiency with time as a xenon light source ages. Coupling efficiency and coupling stability over time are improved, and the central shadowing resulting from an annular focal spot of the prior art is reduced or eliminated. The embodiments of the present invention can be incorporated into any xenon lamp based optical device, such as an ophthalmic illuminator, where optical coupling of a light beam into a small gauge optical fiber is desired.

The present invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims.

What is claimed is:

1. A surgical illumination apparatus, comprising:
a xenon illumination source operable to transmit an optical beam having an uneven annular focal spot;
a beam splitter configured to split the optical beam to yield a plurality of optical beams that travel along a plurality of optical paths; and
a plurality of correcting elements, each correcting element positioned in an optical path between the illumination source and an optical fiber of a plurality of optical fibers, at least two optical fibers having different gauges, each correcting element configured to reshape an optical beam from having an uneven annular focal spot to having a focal spot with a more Gaussian intensity distribution than the uneven annular focal spot, each correcting element comprising a multi-zone lens configured to shift the optical beam from an annulus to an annulus center to increase an amount of the optical beam received at the optical fiber.

2. The surgical illumination apparatus of claim 1, wherein each correcting element comprises an axiconic lens.

3. The surgical illumination apparatus of claim 2, wherein the axiconic lens comprises a multi-zone axicon.

4. The surgical illumination apparatus of claim 2, wherein the axiconic lens comprises a negative axicon.

5. The surgical illumination apparatus of claim 1, wherein each optical fiber has a diameter that is less than or equal to the diameter of a 25-gauge fiber.

6. The surgical illumination apparatus of claim 1, wherein each correcting element comprises a Fresnel lens comprising a series of cone shaped segments.

7. The surgical illumination apparatus of claim 1, the multi-zone lens comprising at least four zones.

8. The surgical illumination apparatus of claim 1, the multi-zone lens comprising at least seven zones.

9. The surgical illumination apparatus of claim 1, the multi-zone lens comprising at least four zones, a first facet tilt angle of a first zone less than a second facet tilt angle of a second zone, the first zone closer to a center of the multi-zone lens than the second zone.

10. The surgical illumination apparatus of claim 1, the multi-zone lens comprising at least four zones, wherein a plurality of facet tilt angles of the four zones from an inner zone to an outer zone are approximately −9 degree, −6 degree, −3 degree, and 1 degree.

11. The surgical illumination apparatus of claim 1, further comprising a coupling lens positioned in the optical path between the correcting element and the optical fiber, the coupling lens configured to focus the reshaped optical beam onto the optical fiber, the coupling lens having a focal length of less than 0.9 inches.

12. The surgical illumination apparatus of claim 1, each correcting element custom-fit to compensate for one or more changes along its optical path.

* * * * *